(12) United States Patent
Jadhav et al.

(10) Patent No.: US 7,819,027 B2
(45) Date of Patent: Oct. 26, 2010

(54) METHOD AND STRUCTURE FOR A PULL TEST FOR CONTROLLED COLLAPSE CHIP CONNECTIONS AND BALL LIMITING METALLURGY

(75) Inventors: Virendra R. Jadhav, Wappingers Falls, NY (US); Vijayeshwar D. Khanna, Millwood, NJ (US); David C. Long, Wappingers Falls, NY (US); David L. Questad, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 574 days.

(21) Appl. No.: 11/766,869

(22) Filed: Jun. 22, 2007

(65) Prior Publication Data

US 2008/0313879 A1 Dec. 25, 2008

(51) Int. Cl.
*G01L 5/24* (2006.01)
(52) U.S. Cl. .................................. 73/862.392
(58) Field of Classification Search ............. 73/862.392
See application file for complete search history.

(56) References Cited

U.S. PATENT DOCUMENTS

| 5,175,609 | A | 12/1992 | DiGiacomo et al. |
| 5,266,522 | A | 11/1993 | DiGiacomo et al. |
| 5,442,239 | A | 8/1995 | DiGiacomo et al. |
| 5,641,913 | A | 6/1997 | Watanabe |
| 5,969,262 | A | 10/1999 | Ino et al. |
| 6,117,695 | A | 9/2000 | Murphy et al. |
| 6,359,452 | B1 * | 3/2002 | Mozzetta ............... 324/754 |
| 6,446,311 | B1 * | 9/2002 | Ueno ................. 24/16 R |
| 6,523,419 | B1 * | 2/2003 | Nonaka et al. .......... 73/827 |
| 6,543,419 | B2 | 4/2003 | Okamoto et al. |
| 7,462,783 | B2 * | 12/2008 | Howard et al. ......... 174/260 |

OTHER PUBLICATIONS

Liu, "Reliability of Surface-mounted Anisotropically Conductive Adhesive Joints", Journal of the Institute of Circuit Technology, 1993, vol. 19 No. 4, Wela Publications Ltd, British Isles.

* cited by examiner

*Primary Examiner*—Lisa M Caputo
*Assistant Examiner*—Octavia Davis
(74) *Attorney, Agent, or Firm*—Cantor Colburn LLP; Katherine Brown

(57) ABSTRACT

A tensile strength testing structure for controlled collapse chip connections (C4) disposed above a substrate includes: a fixture base configured for positioning substrates with C4; a top fixture plate with through hole channels; test pins for insertion through the through hole channels; wherein dimensional tolerances of the substrates are accounted for with openings on at least two sides of the fixture base for positioning the substrates, and during alignment of the top fixture plate through hole channels with the C4 prior to securing the top fixture plate to the fixture base; wherein the test pins are strain hardened metal wires; wherein lower ends of the test pins are joined to the C4 during a solder reflow process; and wherein distal ends of the test pins are pulled in a direction perpendicular to the testing structure to determine the tensile strength of the C4.

5 Claims, 2 Drawing Sheets

METHOD AND STRUCTURE FOR A PULL TEST FOR CONTROLLED COLLAPSE CHIP CONNECTIONS AND BALL LIMITING METALLURGY

TRADEMARKS

IBM® is a registered trademark of International Business Machines Corporation, Armonk, N.Y., U.S.A. Other names used herein may be registered trademarks, trademarks or product names of International Business Machines Corporation or other companies.

BACKGROUND OF THE INVENTION

1. Field of the Invention

This invention relates generally to controlled collapse chip connection, and more particularly to providing a structure and method for implementing a tensile pull test of ball-limiting metallurgies (BLM), to determine the peel strength for Controlled-collapse chip connections (C4).

2. Description of the Background

Controlled-collapse chip connection (C4) is a means of connecting integrated circuit (IC) chips to substrates in electronic packages. C4 is known as a flip-chip technology, in which the interconnections are small solder balls on the bottom side chip surface. C4 technology represents one of the highest density schemes known in the art for chip interconnections. The C4 technology was initially developed in the 1960s and has proven reliable in the semiconductor field. Historically, the PbSn (lead-tin) solder for the formation of the solder ball was evaporated through a metal mask. In the 1990s, electrochemical fabrication of C4 interconnections was introduced. Electroplating is more extendible than evaporation to small C4-pad dimensions, closer pad spacing, larger wafers, and lower-melting solders (which have a higher content of tin (Sn)).

In general, the top layers of an integrated circuit (IC) chip are wiring levels, separated by insulating layers of dielectric material that provide input/output for the device. In C4 structures, the chip wiring is terminated by a plurality of metal films that form the ball-limiting metallurgy (BLM), which is also referred to as under-bump metallurgy (UBM). The ball-limiting metallurgy defines the size of the solder bump after reflow, provides a surface that is wettable by the solder, and that reacts with the solder to provide good adhesion and acceptable reliability under mechanical and heat stress. The BLM also serves as a barrier between the integrated-circuit device and the metals in the interconnection.

FIGS. 1A and 1B are a typical implementation of the C4 manufacturing process. In FIG. 1A an integrated circuit (IC) 100 formed on a base material 102 (for example, silicon) has a solder ball 108 formed for subsequent attachment to a contact pad 112 (see FIG. 1B) on a carrier 114. A BLM 106 constricts the solder flow and aids in the formation of the solder ball 108 (which is formed by reflowing a deposit of solder paste), and serves as a wettable surface and contact for an underlying contact 110 for the IC 100. A passivation layer 104, typically a polymer dielectric, insulates the IC 100, and supports the BLM 106. In FIG. 1B the IC 100 is attached to the contact pad 112 on the carrier 114, by reflowing the solder ball 108. Solder flow is restricted on the carrier 114 by solder dams 116, which outline and define the contact pad 112. A secondary reflow is employed to attach the IC 100 to the contact pad 112 on the carrier 114.

However, despite the widespread use of C4 technology, current solder bump and BLM dimensions have resulted in cracking and metal layer separation at the chip level after attachment to a carrier. In addition, with the introduction of high yield stress lead free solder, low strength low-k dielectric materials, and new BLM structures additional failure modes are occurring, especially in organic flip chips that are governed by peeling (out-of-plane tension) rather than shear forces. However, there is presently no inexpensive and quick way to identify weakness of a particular combination of solder alloy, chip dielectric, and BLM structure without going through an expensive and time consuming chip assembly process. Present testing methods include mechanically holding the C4 solder ball and pulling it. However, this method suffers from major disadvantages, including the possibility of squeezing the C4 ball, and may not work for all solder alloys. The method also does not work if the solder volume is below certain critical volume, which varies with the diameter of the BLM pad. Another method, which involves attaching the chip to a chip carrier and pulling the entire chip suffers from a different disadvantage, wherein the effect of individual laminate design cannot be separated from the test data. Therefore, there is a need for an inexpensive, reliable, and repeatable test for peel strength of C4 chip connections.

SUMMARY OF THE INVENTION

Embodiments of the present invention include a structure and method for tensile strength testing of controlled collapse chip connections (C4) disposed above a substrate, the structure comprising: a fixture base configured for positioning one or more substrates with one or more C4; a top fixture plate with a series of through hole channels therein; one or more test pins for insertion through the series of through hole channels; wherein dimensional tolerances of the one or more substrates are accounted for with openings on at least two sides of the fixture base for positioning the one or more substrates, and during alignment of the top fixture plate through hole channels with the one or more C4 prior to securing the top fixture plate to the fixture base; wherein the one or more test pins are formed from strain hardened metal wires; wherein lower ends of the one or more test pins are joined to the C4 during a solder reflow process; and wherein distal ends of the one or more test pins are pulled in a direction perpendicular to the testing structure to determine the tensile strength of the C4.

A method for testing the peel strength of chip level interconnections in flip chips via a tensile pull of C4 solder balls, the method includes: positioning and securing one or more flip chips with one or more C4 solder ball connections on a fixture base; aligning one or more through hole channels of a top fixture plate with the one or more C4 solder ball connections; securing the top fixture plate to the fixture base; inserting one or more test pins into the one or more through hole channels until the lower ends of the one or more test pins are contacting the one or more C4 solder ball connections; joining the one or more test pins to the one or more C4 solder ball connections; pulling on the one or more test pins to determine the tensile peel strength of the one or more C4 solder ball connections; wherein the one or more test pins are formed by strain hardening a metal wire.

Additional features and advantages are realized through the techniques of the present invention. Other embodiments and aspects of the invention are described in detail herein and are considered a part of the claimed invention. For a better understanding of the invention with advantages and features, refer to the description and to the drawings.

TECHNICAL EFFECTS

As a result of the summarized invention, a solution is technically achieved for an inexpensive, reliable, and repeatable test for peel strength of C4 chip connections. The evaluation of the strength of chip BLM of the C4 connection, and dielectric structures is conducted under tension, wherein the chip, BLM, and solder system are tested independently of the laminate, and the resultant test data can be used for tracking process windows and their variations.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF SPECIFIC EMBODIMENTS

Embodiments of the present invention provide a structure and method for testing the peel strength of chip level interconnections in flip chips via a tensile pull of a C4 solder ball. The peel strength testing is facilitated by a test pin created with a strain hardening procedure, and which is wetted to the C4 solder ball on a substrate secured and located by a test fixture with standard reflow procedures. The peel strength test of embodiments of the present invention is inexpensive, reliable, and repeatable, and provides a way to evaluate the strength of chip BLM and dielectric structures in tension, while providing the ability to test the chip, BLM, and solder system independently of the laminate. Embodiments of the invention facilitate the evaluations of solder wettability, the strengths of new solder/BLM interfaces, and the strengths of low dielectric constant inter layer dielectric (low-k ILD) materials. The resultant peel strength test data can be used for tracking process windows and their variations for manufacturing process control.

Figures 1A, 1B:
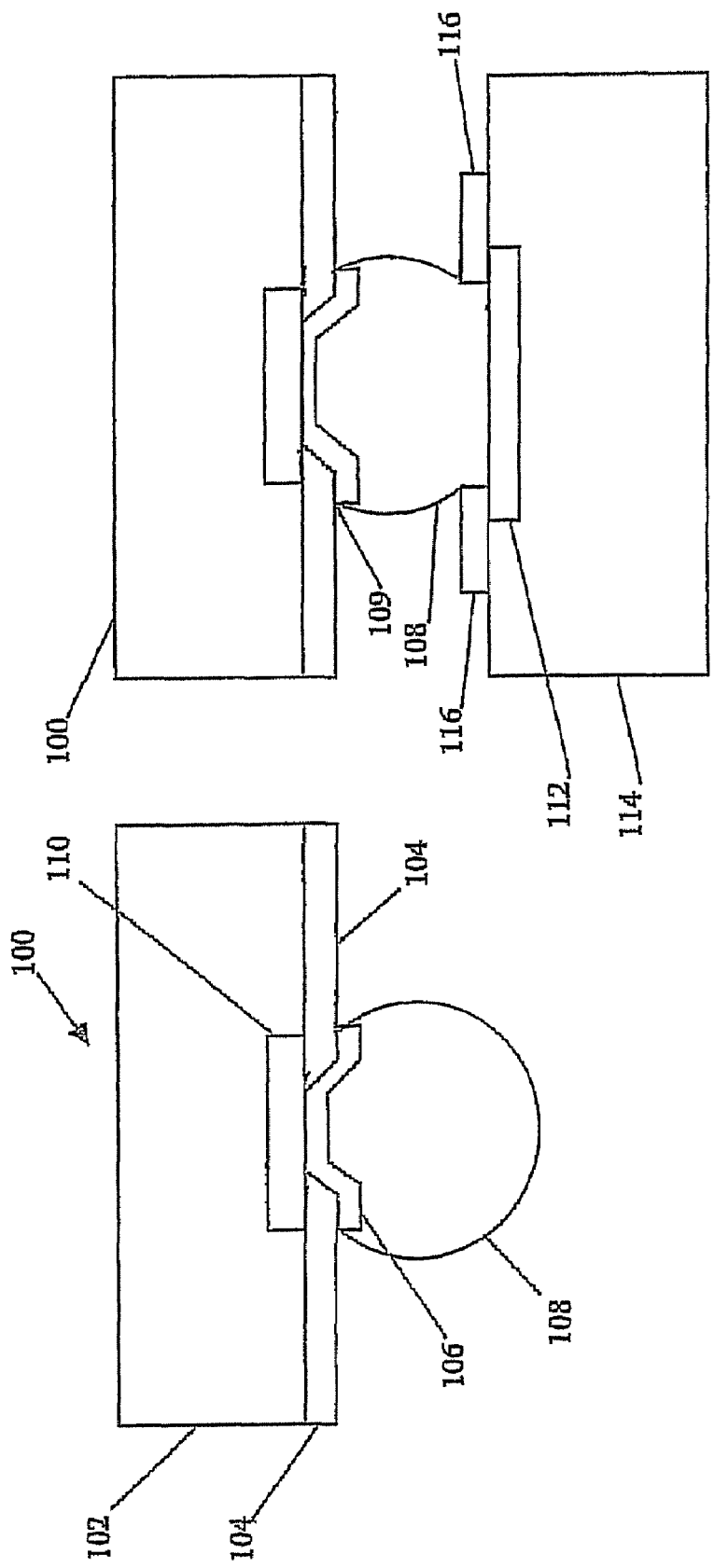
FIG. 1A is a typical cross sectional view of a solder ball formed on ball limiting metallurgy attached to an integrated circuit.
FIG. 1B is a typical cross sectional view of an integrated circuit joined to a carrier employing controlled-collapse chip connection (C4).
Figure 2:
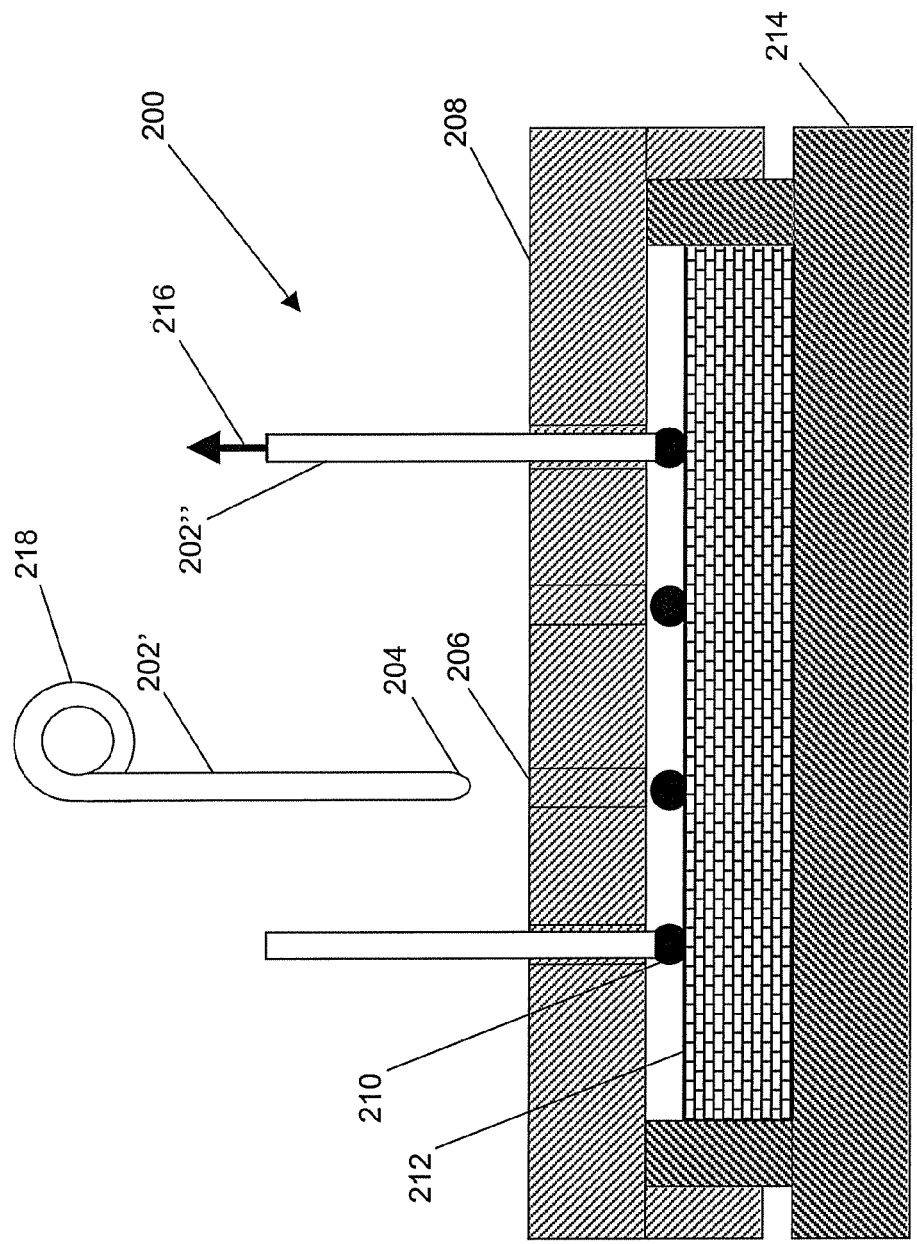
FIG. 2 is a cross sectional view of a test fixture and test pins with an integrated circuit with C4 configured for testing peel strength of the C4 according to an embodiment of the present invention.

FIG. 2 is a cross sectional view of a test fixture system 200 and test pins 202, along with an integrated circuit (IC) 212 chip with C4 solder balls 210, configured for testing peel strength of the C4 solder balls 210 and their associated BLM (not shown) according to an embodiment of the present invention. The test fixture system 200 includes a fixture base 214, with locating and securing features for aligning one or more IC 212 chip substrates to be tested. Due to the fact that the tolerances of the IC 212 chips, following their separation (dicing) from the silicon wafer from which they are formed, are on the same order as the C4 solder ball 210 pitch (distances between C4 connections), it is generally difficult to have rigid fixtures. However, embodiments of the fixture system 200 of the present invention accommodate for the IC 212 chip tolerances with at least two open sides to position the IC 212 chip into a designated area on the surface of the fixture base 214. The tolerances are then accommodated while placing the top fixture plate 208. One or more channels 206 formed in the top fixture plate 208 are aligned with the C4 solder balls 210 prior to securing the top fixture plate 208 to the fixture base 214. The channels 206 act as guides for the test pins 202 during their attachment to the C4 solder balls 210, and the channels 206 are orthogonal to the C4 solder balls 210 and the IC 212 chip surface to facilitate the pull testing of the C4 solder balls. The top fixture plate 208 is secured to the fixture base 214, by a series of bolts or screws (not shown), or by clamps (not shown).

The test pins 202 are formed by strain hardening metal wire. The metal wire is pulled straight in order to reduce the diameter of the wire in the neck section 204 where it breaks off from the wire spool supply, thereby forming a tapered "bullet" shape at the end. The tapered end 204 of the strain hardened metal wire is approximately the size of the C4 solder ball 210 to which it attaches. The tapered end 204 can also be sanded to a flat end. The distal end of the test pin 202' may be formed in a loop 218 to facilitate the pull test mechanism (not shown). The test pins 202 may be created just prior to reflow, thereby avoiding oxidation and contamination issues. Solder wetting of the tapered end 204, with a eutectic solder, facilitates the attachment of the test pin 202 to high melt C4 solders. Standard reflow procedures may be used for attaching the test pins 202 to the C4 solder balls 210. Test pin 202" is shown already attached to a C4 solder ball 210. The arrow 216 indicates that the test pin 202" is under upward tension, and the tensile peel strength of the C4 solder ball 210 is under test.

In an example embodiment of the present invention for a test a tensile strength test conducted on a "4 on 8" C4 configuration, the nominal diameter of the C4 pad is 4 mils (approximately 100 micrometers), and the spacing between C4s is about 8 mils (approximately 200 microceters). The nominal diameter of the channel 206 in the top plate 208 is about 11 mils (approximately 275 micrometers), The test pin 202' is about 10 mils (approximately 250 micrometers) diameter near the far end where it is looped 218. The tapered end 204 that gets soldered typically narrows down to about 3 mils (approximately 75 micrometers). The channel diameter, test pin and C4 dimensions are configured to allow a detached solder ball to be pulled through the channels 206 and completely out of the top plate 208, with the fractured surface staying intact in most cases. The intact nature of the fractured surface provides the opportunity to examine both the pin side and the chip side of the failed surface. For tensile strength tests conducted on "3 on 6" C4s, the C4 pad diameter is about 3 mils, spacing between C4s is about 6 mils, and the dimension of the channel is approximately 9 mils with a test pin max diameter of about 8 mils, going down to about 2-3 mils at the soldered end. As in the case of the "4 on 8" C4 configuration, the BLM fracture remains intact for further analysis.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A tensile strength testing structure for controlled collapse chip connections (C4) disposed above a substrate comprising:
- a fixture base configured for positioning one or more substrates with one or more C4;
- a top fixture plate with a series of through hole channels therein;
- one or more test pins for insertion through the series of through hole channels;
- wherein dimensional tolerances of the one or more substrates are accounted for with openings on at least two sides of the fixture base for positioning the one or more substrates, and during alignment of the top fixture plate through hole channels with the one or more C4 prior to securing the top fixture plate to the fixture base;
- wherein the one or more test pins are strain hardened metal wires;
- wherein lower ends of the one or more test pins are joined to the C4 during a solder reflow process;
- wherein distal ends of the one or more test pins are configured to be pulled in a direction perpendicular to the testing structure to determine the tensile strength of the C4;
- means for pulling and stretching one or more of the wires until one or more of the wires breaks to facilitate the strain hardening;
- wherein the area of the break forms the lower end of the test pin; and
- wherein the surface area of the break approximates the size of the C4 that the test pin will attach to.

2. The structure of claim 1, wherein the one or more test have lower ends that are tapered.

3. The structure of claim 1, wherein the one or more test pins have lower ends that are balled.

4. The structure of claim 1, wherein the one or more test pins have lower ends that are flat ended.

5. The structure of claim 1, wherein the distal ends of the one or more test pins have a loop to facilitate the pulling.

* * * * *